US011016061B2

(12) United States Patent
Itoi et al.

(10) Patent No.: US 11,016,061 B2
(45) Date of Patent: May 25, 2021

(54) METHOD AND APPARATUS FOR EVALUATING DAMAGE TO MAGNETIC LINEAR BODY

(71) Applicant: TOKYO ROPE MANUFACTURING CO., LTD., Tokyo (JP)

(72) Inventors: Hiroaki Itoi, Tokyo (JP); Hironori Kanemaru, Tokyo (JP); Yuuta Hashime, Tokyo (JP)

(73) Assignee: TOKYO ROPE MANUFACTURING CO., LTD., Tokyo (JP)

( * ) Notice: Subject to any disclaimer, the term of this patent is extended or adjusted under 35 U.S.C. 154(b) by 178 days.

(21) Appl. No.: 16/427,670

(22) Filed: May 31, 2019

(65) Prior Publication Data

US 2019/0285586 A1     Sep. 19, 2019

Related U.S. Application Data

(63) Continuation of application No. PCT/JP2016/085747, filed on Dec. 1, 2016.

(51) Int. Cl.
*G01R 33/00* (2006.01)
*G01R 33/10* (2006.01)
(Continued)

(52) U.S. Cl.
CPC ............ *G01N 27/83* (2013.01); *G01N 27/80* (2013.01); *G01N 27/82* (2013.01); *G01N 27/902* (2013.01);
(Continued)

(58) Field of Classification Search
CPC ...... G01D 5/145; G01D 11/245; G01D 3/022; G01D 5/202; G01R 33/093; G01R 33/09;
(Continued)

(56) References Cited

U.S. PATENT DOCUMENTS

| 6,119,526 A | 9/2000 | Reigstad et al. |
| 2008/0061635 A1* | 3/2008 | Saitou ............... H01F 41/0253 310/13 |

(Continued)

FOREIGN PATENT DOCUMENTS

| JP | S5454086 A | 4/1979 |
| JP | S62276454 A | 12/1987 |

(Continued)

OTHER PUBLICATIONS

Korean Intellectual Property Office Notice of Preliminary Rejection; dated May 15, 2020; 6 pgs.; English Language Translation; 5 pgs.

*Primary Examiner* — Raul J Rios Russo
(74) *Attorney, Agent, or Firm* — Dickinson Wright PLLC

(57) ABSTRACT

A damage evaluation apparatus, which is used on a concrete structure having an embedded tendon to be evaluated for damage. The damage apparatus includes a magnetizer for generating magnetic force, and a detector for detecting a change in magnetism produced from a damaged area of the tendon. The magnetizer includes an excitation coil; an iron core passed through a center hole of the excitation coil; and a pair of columnar yokes connected to respective ends of the iron core and each extending toward the surface of the concrete. By passing an electric current through the excitation coil, a magnetic circuit is formed by the yoke shaft, the pair of columnar yokes, and the tendon over a range thereof situated between a pair of plate-shaped yokes. Current that flows through the excitation coil is controlled such that the magnetic flux density of the tendon is rendered constant.

8 Claims, 10 Drawing Sheets

(51) Int. Cl.

| | | |
|---|---|---|
| *G01N 27/83* | (2006.01) | |
| *G01N 27/80* | (2006.01) | |
| *G01N 27/9013* | (2021.01) | |
| *G01N 33/38* | (2006.01) | |
| *G01R 33/02* | (2006.01) | |
| *G01R 33/12* | (2006.01) | |
| *G01V 3/10* | (2006.01) | |
| *G01N 27/82* | (2006.01) | |
| *G01R 33/09* | (2006.01) | |
| *G01R 31/28* | (2006.01) | |
| *G01R 33/06* | (2006.01) | |
| *G01D 5/14* | (2006.01) | |
| *G01D 11/24* | (2006.01) | |
| *G01D 3/02* | (2006.01) | |
| *G01D 5/20* | (2006.01) | |

(52) U.S. Cl.
CPC ....... *G01N 33/383* (2013.01); *G01R 31/2829* (2013.01); *G01R 33/02* (2013.01); *G01R 33/06* (2013.01); *G01R 33/09* (2013.01); *G01R 33/093* (2013.01); *G01R 33/12* (2013.01); *G01V 3/104* (2013.01); *G01D 3/022* (2013.01); *G01D 5/145* (2013.01); *G01D 5/202* (2013.01); *G01D 11/245* (2013.01)

(58) Field of Classification Search
CPC .... G01R 31/2829; G01R 33/06; G01R 33/02; G01R 33/12; G01R 33/0094; G01R 33/072; G01N 27/83; G01N 27/82; G01N 27/80; G01N 27/902; G01N 33/383; G01V 3/104; G01V 3/081
USPC .................................. 324/200–263
See application file for complete search history.

(56) References Cited

U.S. PATENT DOCUMENTS

2010/0254565 A1* 10/2010 Saitou ................ H01F 41/0253
381/400
2015/0028975 A1* 1/2015 Kamiunten ........... F16F 15/035
335/295

FOREIGN PATENT DOCUMENTS

| JP | 03-262957 A | 11/1991 |
|---|---|---|
| JP | 2002005896 A | 1/2002 |
| JP | 2005292111 A | 10/2005 |
| JP | 2005326152 A | 11/2005 |
| JP | 2006300730 A | 11/2006 |
| JP | 3163378 U | 10/2010 |
| JP | 2014062745 A | 4/2014 |

* cited by examiner

METHOD AND APPARATUS FOR EVALUATING DAMAGE TO MAGNETIC LINEAR BODY

CROSS REFERENCE TO RELATED APPLICATIONS

This application is a Continuation Application of PCT International Application No. PCT/JP2016/085747 filed on Dec. 1, 2016, the entire disclosure of the application being considered part of the disclosure of this application and hereby incorporated by reference.

TECHNICAL FIELD

The present invention relates to a method and apparatus for evaluating damage (state of deterioration) of a magnetic linear body, typically a magnetic linear body that is embedded in concrete. The linear body includes a cable, rope, strand, cord, wire, rod, pole, shaft or other object in a form extending continuously in one direction, and also includes not only twisted objects but also objects merely bundled together or alone. Further, size of diameter and cross-sectional shape of the body do not matter. The term "magnetic linear body" signifies a linear body produced from a magnetic material, typically a ferromagnetic material.

BACKGROUND ART

Japanese Patent Application (Laid-Open No. 2002-5896) discloses a wire-rope damage detector which attaches a probe coil so as to surround a wire rope.

Here the assumption is that a wire rope to be inspected by the damage inspection apparatus described in the JP Patent Application is a wire rope capable of being surrounded by a probe coil, namely a wire rope exposed to the outside. With the damage detector described in the JP Patent Application, a wire rope that has been embedded in concrete cannot be inspected as is embedded in the concrete.

DISCLOSURE OF THE INVENTION

An object of the present invention is to arrange it so that a magnetic linear body embedded in concrete can be inspected as is embedded in the concrete.

A further object of the present invention is to so arrange it that a signal waveform representing damage can be normalized even if there is a variation in distance from a damage evaluation apparatus to a magnetic linear body embedded in concrete.

A method of evaluating damage to a magnetic linear body according to the present invention, comprising: moving a damage evaluation apparatus along the magnetic linear body; on a concrete structure in which the magnetic linear body, which is to undergo evaluation of damage, is embedded; the apparatus including a magnetizer for generating magnetic force, and a detector for detecting an amount of change in magnetism produced from a damaged area of the magnetic linear body magnetized by the magnetic force generated by the magnetizer; forming a magnetic circuit by passing an electric current through an excitation coil by the magnetizer, wherein the magnetizer includes the excitation coil as well as a yoke shaft inserted into a center hole of the excitation coil; and a pair of columnar yokes connected to respective ones of both ends of the yoke shaft and each extending toward the surface of the concrete, the magnetic circuit including the yoke shaft, the pair of columnar yokes, and the magnetic linear body over a range thereof situated between the pair of columnar yokes; and controlling the electric current, which is passed through the excitation coil, in dependence upon embedded depth of the magnetic linear body within the concrete structure so as to hold constant a magnetic flux density in the magnetic linear body over the range thereof situated between the pair of columnar yokes. Damage includes abrasion, corrosion, severance and the like.

An apparatus for evaluating damage to a magnetic linear body according to the present invention is used upon being placed on a concrete structure in which the magnetic linear body, which is to undergo evaluation of damage, is embedded, and the apparatus includes a magnetizer for generating magnetic force, and a detector for detecting an amount of change in magnetism produced from a damaged area of the magnetic linear body magnetized by the magnetic force generated by the magnetizer; the apparatus having a moving device, which includes a movement amount sensor, for moving the damage evaluation apparatus along the magnetic linear body, and a power supply device for supplying the magnetizer with electric current; wherein the magnetizer includes an excitation coil, a yoke shaft inserted into a center hole of the excitation coil, and a pair of columnar yokes connected to respective ones of both ends of the yoke shaft and each extending toward the surface of the concrete, and passes an electric current through the excitation coil, whereby a magnetic circuit is formed by the yoke shaft, the pair of columnar yokes, and the magnetic linear body over a range thereof situated between the pair of columnar yokes; the apparatus further having a control unit for controlling the electric current, which is passed through the excitation coil of the magnetizer from the power supply device, in dependence upon embedded depth of the magnetic linear body within the concrete structure so as to hold constant a magnetic flux density in the magnetic linear body over the range thereof situated between the pair of columnar yokes.

In accordance with the present invention, a magnetic circuit is formed that includes in its path the magnetic linear body within the concrete. If the magnetic linear body sustains a reduction in cross-sectional area due to abrasion or corrosion or develops a gap due to severance thereof, magnetic resistance in the magnetic circuit increases and there is a change (reduction) in the magnetic flux that flows through the magnetic circuit. Damage (deterioration) produced in the magnetic linear body embedded in the concrete can be evaluated based upon the change in magnetic flux detected by the magnetic flux detector.

Since the magnetic linear body is embedded in concrete, gaps (portions where there are separations in the magnetic circuit due to the intervention of the concrete) exist between the pair of columnar yokes and the magnetic linear body. The permeability of concrete is comparatively small (substantially the same value as that of the permeability of air) and a decline in the magnetic flux that flows through the magnetic circuit between the pair of columnar yokes and magnetic linear body cannot be avoided. The gaps between the respective pair of columnar yokes and the magnetic linear body can be considered resistance in the magnetic circuit. The longer the gaps, the greater the resistance in the magnetic circuit.

In accordance with the present invention, the electric current that flows through the excitation coil is controlled in dependence upon the depth at which the magnetic linear body is embedded within the concrete structure, and the magnetic flux density (strength of the magnetic field) in the magnetic linear body over the range thereof situated between the pair of columnar yokes (the magnetic linear body over the range thereof that forms the magnetic circuit) is held constant. A fluctuation in amount of change in magnetism ascribable to the embedded depth of the magnetic linear body, namely the length of the gaps, can be cancelled. A signal waveform representing damage is normalized even if there is a variation in distance from the damage evaluation apparatus to the magnetic linear body embedded in the concrete. This makes it possible to ascertain the extent of damage more accurately.

Preferably, the detector is a search coil wound around at least one of the pair of columnar yokes. The search coil outputs a voltage conforming to the magnetic flux (number of magnetic flux linkages) that flows through the magnetic circuit. This makes it possible to sense a change in magnetic flux that arises from damage sustained by the magnetic linear body embedded in the concrete.

In an embodiment, the damage evaluation apparatus has a position detecting device for detecting the position of the damage evaluation apparatus relative to the magnetic linear body, path of movement of the damage evaluation apparatus being decided in accordance with an output from the position detecting device. In an embodiment, the position detecting device is constituted by search coils wound around respective ones of the pair of columnar yokes. Magnetic flux that flows through the columnar yokes is maximized when the magnetic linear body is situated directly below the columnar yokes. Based upon the output signals from the two search coils, therefore, the position of the magnetic linear body embedded in the concrete can be sensed and the path of travel of the damage evaluation apparatus situated at the position of the magnetic linear body can be decided.

DETAILED DESCRIPTION OF THE INVENTION

Figure 1:
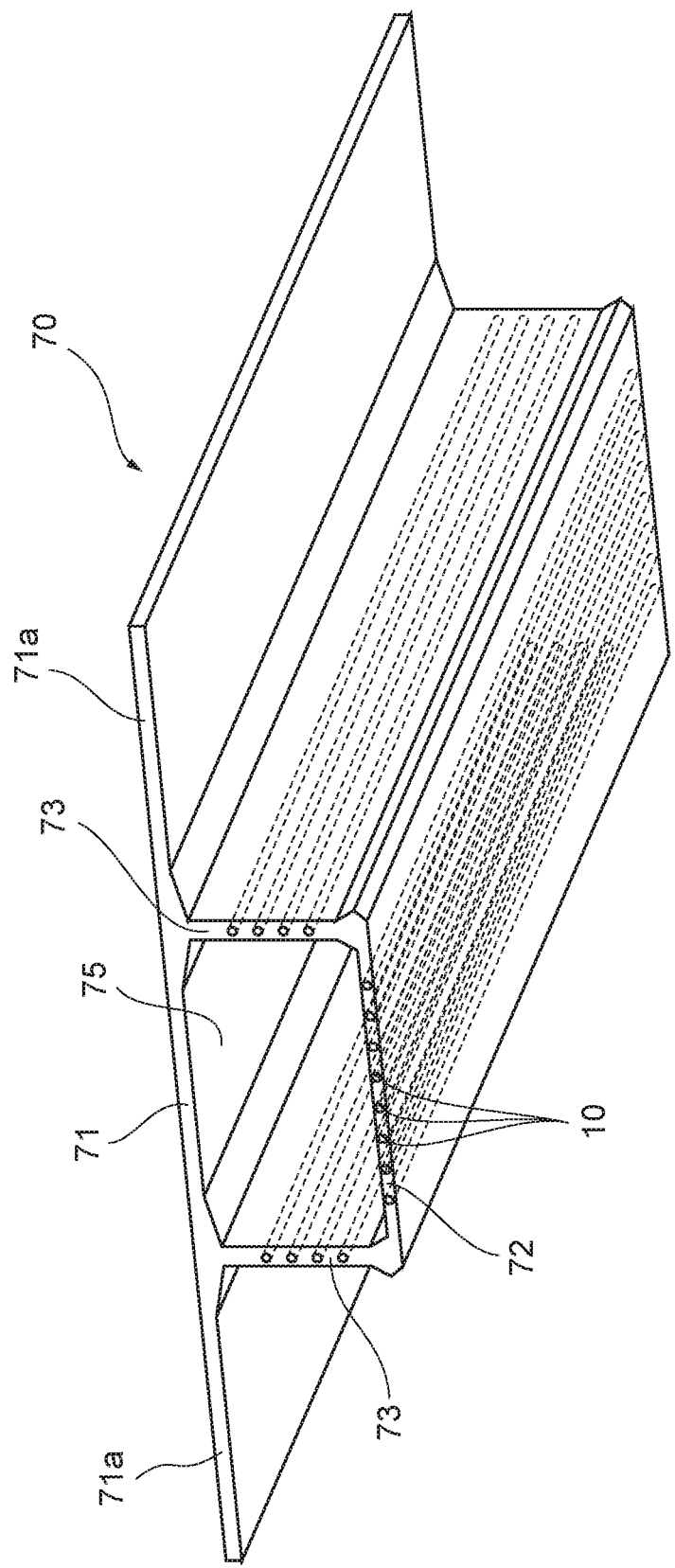
FIG. 1 is a perspective view in which a box girder constituting a concrete box-girder bridge is seen from below.

FIG. 1 is a perspective view in which a box girder constituting a concrete box-girder bridge is seen from below.

The concrete box-girder bridge is fabricated by joining multiple concrete girders, made of concrete, along the axial direction of the bridge. A girder 70 is composed of an upper flange 71, a lower flange 72 provided below the upper flange 71 substantially in parallel with the upper flange 71 and spaced away therefrom, and webs 73 connecting respectively each side portion of the upper flange 71 and lower flange 72. A space 75 extending along the axial direction of the bridge and enclosed by the upper flange 71, lower flange 72 and webs 73 on both sides is large enough to allow entry of a person so that the concrete box-girder bridge (girder 70) can be inspected from within the space 75. Both sides of the upper flange 71 extend outward sideways from the respective sides, the width of the concrete box-girder bridge being decided by the upper flange 71 and extended portions 71a on both its sides. In general, handrails (not shown) are provided along side edges of the extended portions 71a on the upper surface thereof. The surface of the upper flange 71 and extended portions 71a generally is surfaced with asphalt, and vehicles and pedestrians or the like travel on the asphalt-surfaced upper flange 71 and extended portions 71a.

Multiple steel tendons 10 are embedded inside the concrete lower flange 72 and webs 73, which constitute the girder 70, and they extend along the axial direction of the bridge. The tendons 10, which are used to impart the concrete with compressive stress, are made of steel wire, steel rods or stranded steel wire, these being ferromagnetic bodies the main component of which is iron.

Figure 2:
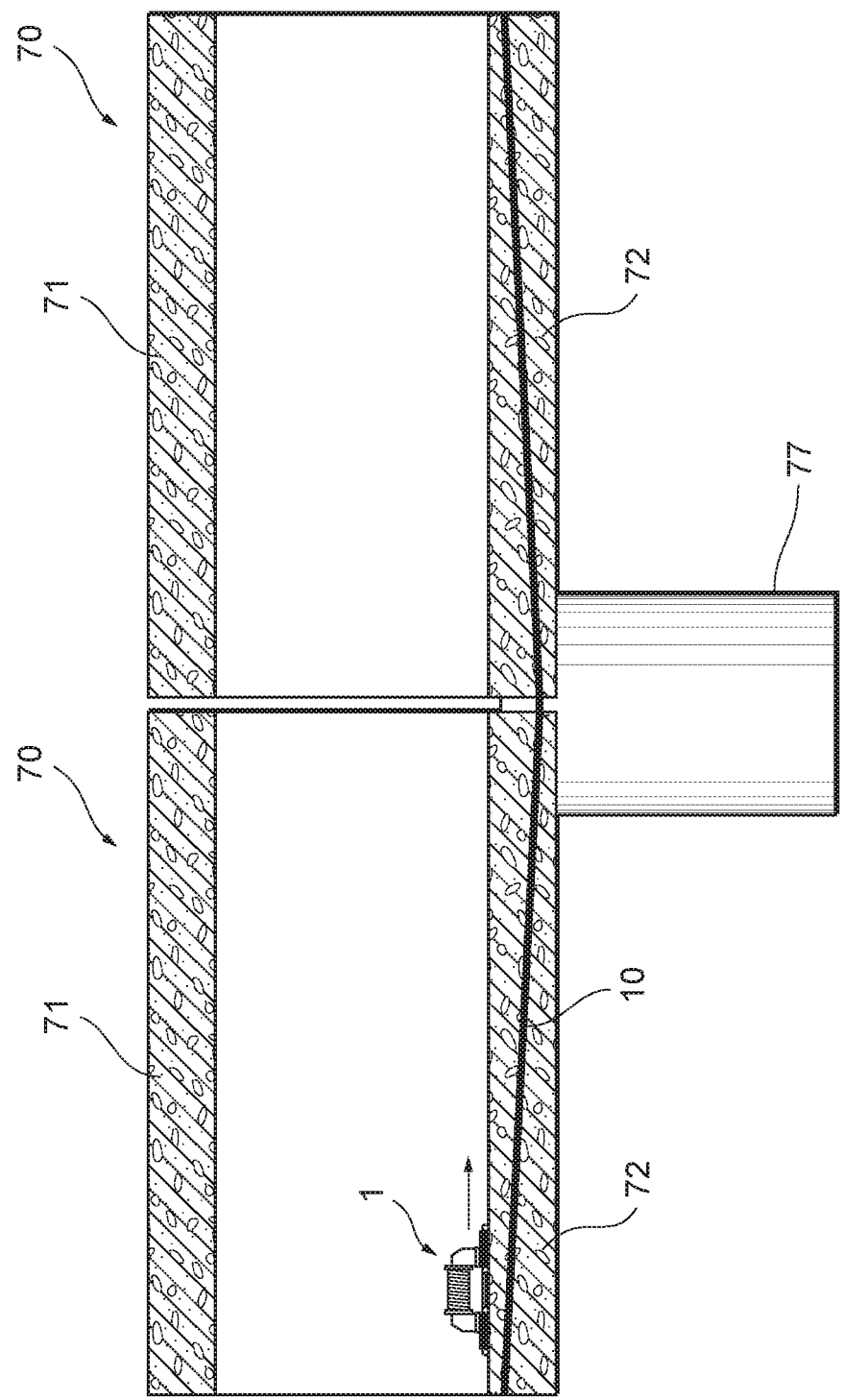
FIG. 2 is a longitudinal sectional view of the concrete box-girder bridge.

FIG. 2 illustrates the longitudinal cross-section of the concrete box-girder bridge together with a damage evaluation apparatus 1. In order to facilitate understanding, the thicknesses of the upper flange 71 and lower flange 72 and the diameter of the tendon 10 are emphasized in the illustration. Further, although FIG. 2 shows a concrete box-girder bridge constructed by aligning two of the girders 70, in general the concrete box-girder bridge is constructed from a greater number of the girders 70.

A bridge pier 77 is provided on the lower surface of the two girders 70 intermediate the girders aligned along the axial direction of the bridge, and the concrete box-girder bridge is supported by the bridge pier 77.

As mentioned above, multiple tendons 10 for imparting the concrete with compressive stress are embedded in the lower flange 72 of the girder 70 (one of the multiple tendons 10 is shown in FIG. 2). The tendon 10 has a length that exceeds the length, in the axial direction of the bridge, of the multiple girders 70 aligned along the axial direction of the bridge. One tendon 10 is embedded spanning multiple girders 70.

There are instances where the tendon 10 is embedded obliquely in the thickness direction (depth direction) of the concrete in order to impart the concrete with compressive stress uniformly in the thickness direction. FIG. 2 illustrates the manner in which the tendon 10 has been embedded obliquely in the thickness direction of the lower flanges 72 constituting the girders 70.

The tendons 10 embedded in the concrete are inspected in the embedded state as is one at a time by the damage evaluation apparatus 1.

Figure 3:
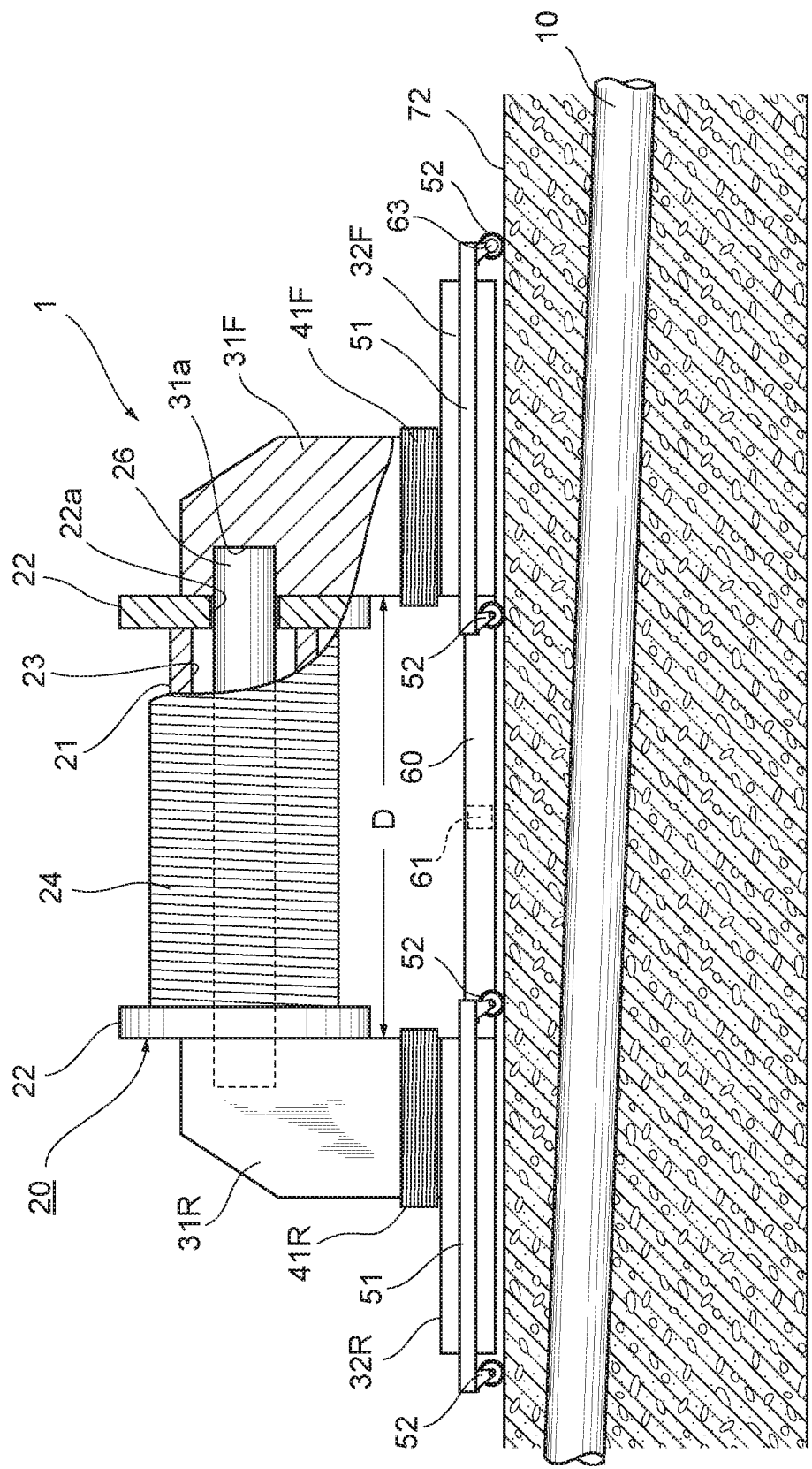
FIG. 3 is a partially cut-away side view of a damage evaluation apparatus.
Figure 4:
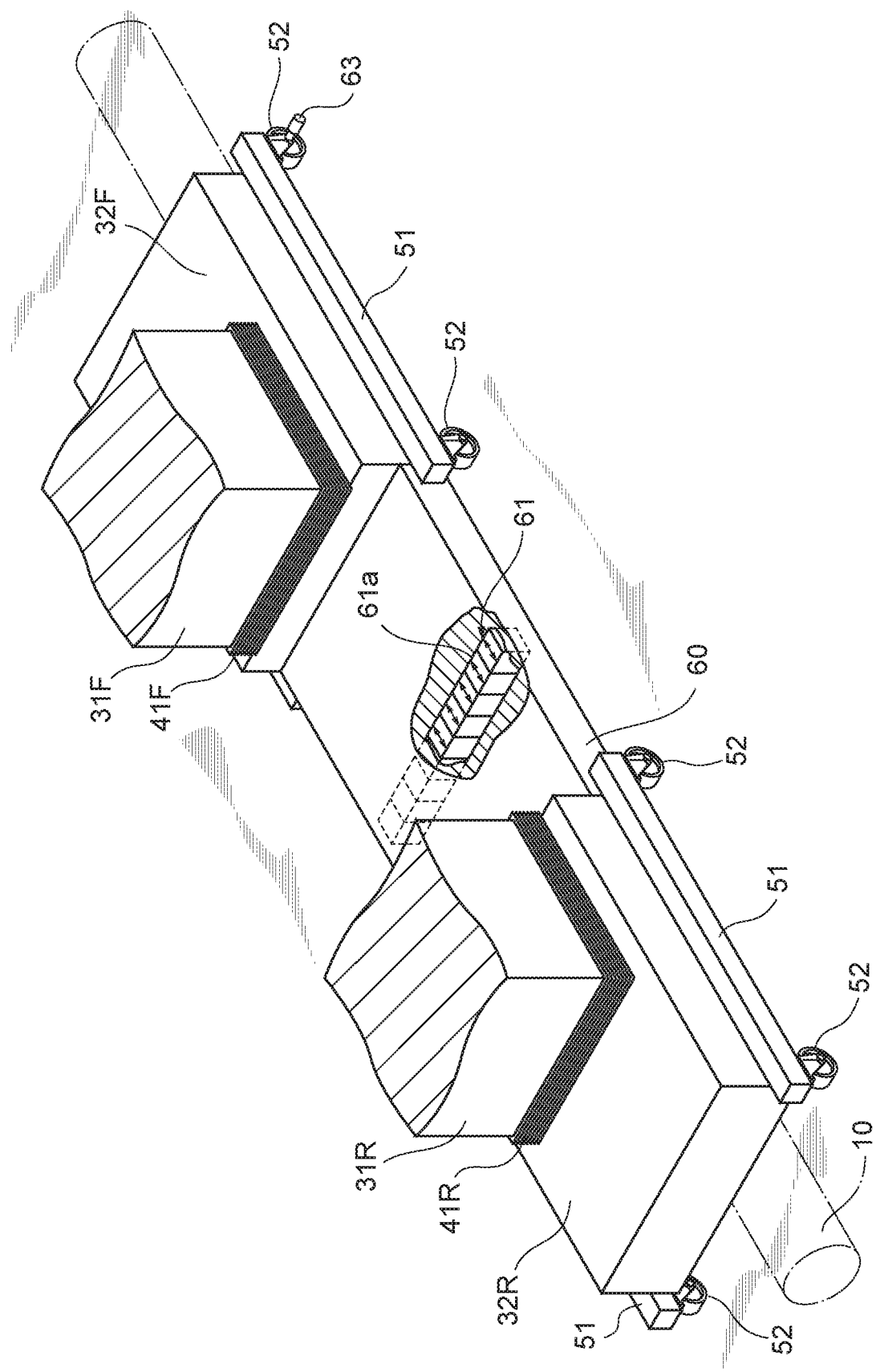
FIG. 4 is an enlarged perspective view partially illustrating a lower portion of the damage evaluation apparatus.

FIG. 3 illustrates the damage evaluation apparatus, partially cut away and seen from the side, placed on the surface of the concrete (on the concrete lower flange 72 constituting the above-mentioned girder 70) in which the tendon 10 has been embedded. FIG. 4 is an enlarged perspective view partially illustrating a lower portion of the damage evaluation apparatus. With reference to FIG. 3, the damage evaluation apparatus 1 is equipped with a magnetizer 20 for magnetizing a portion of tendon 10, which is embedded in the concrete, in order to form a magnetic circuit that includes the tendon 10. The magnetizer 20 has a cylindrical bobbin 21; annular flanges 22 secured to respective ones of both ends of the bobbin; an excitation coil 24 wound around the peripheral surface of the bobbin 21 over the entirety of the bobbin between the annular flanges 22 on both ends thereof; an iron core (yoke shaft) 26, which has a circular cross-section, passed through a center hole 23 of the bobbin 21; a pair of columnar yokes 31F, 31R removably secured to the outer surface of respective ones of the two annular flanges 22 and extending downward from both ends of the bobbin 21 (excitation coil 24); and plate-shaped yokes 32F, 32R removably secured to the columnar yokes 31F, 31R, respectively, at a distal end (lower face) thereof.

The damage evaluation apparatus 1 is placed on the concrete surface so as to bring into agreement the axial direction of the excitation coil 24, which constitutes the magnetizer 20, and the longitudinal direction (axial direction) of the tendon 10 to be inspected, and in such a manner that the excitation coil 24 and tendon 10 are aligned one above the other. The damage evaluation apparatus 1 is adapted so as to be movable along a straight line, as will be described later. Preferably, rails (not shown), which are for moving the damage evaluation apparatus 1 directly above the tendon 10 and along the tendon 10 embedded in the concrete, are placed on the concrete surface in advance.

The center of each of the annular flanges 22 has a through-hole 22a that communicates with the center hole 23 of the bobbin 21. The iron core 26 passes through the center hole 23 of the bobbin 21 and through the through-holes 22a of the annular flanges 22 on both sides, and has such a length that it protrudes to the exterior of the annular flanges 22 on both sides. The iron core 26 is magnetized by a magnetic field generated by passing an electric current through the excitation coil 24.

The columnar yokes 31F, 31R in this embodiment are prism-shaped and removably secured at their upper side face to the outer surface of the respective annular flanges 22. The side face of each of the columnar yokes 31F, 31R secured to the annular flanges 22 is formed to have a cylindrical recess 31a. The ends of the iron core 26 are inserted into the respective cylindrical recesses 31a.

As mentioned above, the columnar yokes 31F, 31R extend downwardly (in the direction toward the concrete surface) from both sides of the bobbin 21 (excitation coil 24), and the plate-shaped yokes 32F, 32R are removably secured to the distal end (lower face) thereof. With reference to FIG. 4, the plate-shaped yokes 32F, 32R are rectangular when viewed in a plane and have spread in the horizontal direction, i.e., along the surface of the concrete.

By way of example, permalloy (an Fe—Ni alloy) having a high permeability or permendur (an Fe—Co alloy) exhibiting a high saturation magnetic flux density is used as the material of the columnar yokes 31F, 31R and plate-shaped yokes 32F, 32R. The columnar yokes 31F, 31R and plate-shaped yokes 32F, 32R may consist of the same material or of different materials. Naturally, comparatively inexpensive carbon steel for mechanical structures can also be used. The size of the magnetomotive force generated by the excitation coil 24 may be adopted as the criterion for selecting the material of the columnar yokes 31F, 31R and plate-shaped yokes 32F, 32R. For example, a material having a high permeability might be selected when the excitation coil 24 (bobbin 21) is small in size and cannot generate a large magnetomotive force, and it is conceivable to select a material exhibiting a high saturation flux density in a case where the excitation coil 24 (bobbin 21) is large in size and can generate a large magnetomotive force.

With reference to FIGS. 3 and 4, frames 51 are secured to the end faces on both sides of each of the plate-shaped yokes 32F, 32R, and casters 52 are rotatably attached to both ends of each frame 51. The damage evaluation apparatus 1 can be moved linearly along the concrete surface by virtue of the casters 52. The damage evaluation apparatus 1 can also be made to turn by virtue of the casters 52.

A rotary encoder 63 (the rotary shaft thereof) is mounted on the rotary shaft of one of the multiple casters 52, the amount of movement of the damage evaluation apparatus 1 being measured by the rotary encoder 63.

The tendon 10 to be inspected is situated below the bottom face of each of the plate-shaped yokes 32F, 32R (the face facing the concrete surface). A magnetic circuit passing through the excitation coil 24 (iron core 26), the columnar yoke 31F, the plate-shaped yoke 32F, the tendon 10, which is a ferromagnetic body, the plate-shaped yoke 32R, and the columnar yoke 31R is formed by the magnetizer 20, with which the damage evaluation apparatus 1 is equipped, and a portion of the tendon 10.

Since the tendon 10 is embedded in the concrete, the plate-shaped yokes 32F, 32R are not connected to the tendon 10 and therefore gaps exist between the yokes and tendon. The gaps can be considered as magnetic resistance in the magnetic circuit.

If we let F represent the magnetomotive force of the excitation coil 24 having the iron core 26, f the total magnetic flux and R the magnetic resistance of the magnetic circuit, then the total flux f will be expressed by Equation 1 below:

$$f=F/R \qquad \text{Equation 1}$$

If we let L represent the gap length and A the gap cross-sectional area, then the magnetic resistance R will be given by Equation 2 below:

$$R=L/\mu A \qquad \text{Equation 2}$$

where $\mu$ is the permeability of the magnetic path of the gaps, which here is the permeability of the concrete and the very small clearance (air) between the plate-shaped yokes 32F, 32R and the surface of the concrete.

In view of Equation 2, the larger the gap cross-sectional area A, the smaller the magnetic resistance R in the magnetic circuit can be made. As set forth above, the spread-out plate-shaped yokes 32F, 32R are provided on the distal end of the respective columnar yokes 31F, 31R, and thus the gaps are imparted with a large cross-sectional area. As a result, it is possible to reduce the magnetic resistance in the magnetic circuit formed by the excitation coil 24 (iron core 26), the columnar yoke 31F, the plate-shaped yoke 32F, the tendon 10, the plate-shaped yoke 32R, and the columnar yoke 31R, and loss of magnetomotive force in the excitation coil 24 can be reduced. Further, by enlarging the gap cross-sectional area by using the plate-shaped yokes 32F, 32R, the weight of the damage evaluation apparatus 1 can be reduced in comparison with a case where the gap cross-sectional area is enlarged as by using columnar yokes 31F, 31R that are thick.

Further, with the damage evaluation apparatus 1, one of the columnar yokes 31F, 31R (plate-shaped yokes 32F, 32R) forms an N pole and the other forms an S pole. The fact that the spacing between the opposing surfaces of the columnar yokes 31F, 31R (plate-shaped yokes 32F, 32R), namely a distance D between the poles, is made sufficiently greater than the gap length is also a characterizing feature. Since the magnetic resistance between the magnetic poles (between the plate-shaped yokes 32F, 32R and between the columnar yokes 31F, 31R) can be made greater than the magnetic resistance in the gaps between the plate-shaped yokes 32F, 32R and tendon 10, the magnetic flux that flows directly between the magnetic poles can be eliminated or made small. This also contributes to reducing the loss of magnetomotive force in the magnetic circuit that includes the tendon 10. It is preferred to assure a pole-to-pole distance D that is several times, for example three to ten times, the gap length.

With reference to FIGS. 3 and 4, search coils 41F, 41R are wound around the respective columnar yokes 31F, 31R in the vicinity of the base end of each. If the tendon 10 experiences a reduction in cross-sectional area due to abrasion or corrosion or develops a gap due to severance, magnetic resistance in the above-mentioned magnetic circuit increases. An increase in magnetic resistance causes a change in magnetic flux that flows through the magnetic circuit. Since the search coils 41F, 41R are wound around the columnar yokes 31F, 31R that form the magnetic path of the magnetic circuit, the magnetic flux that flows through the magnetic circuit interlinks with the search coils 41F, 41R, and the search coils 41F, 41R generate electromotive force conforming to the change in the magnetic flux linkage. Damage that has occurred in the tendon 10 can be evaluated quantitatively based upon output signals from the search coils 41F, 41R and damage evaluation, which is of total-flux measurement type using so-called "return flux", can be carried out. The average value of the output signals from the search coils 41F, 41R may be used in evaluating damage, or the two search coils 41F, 41R may be differentially connected and a single output signal from one of the two search coils 41F, 41R used in evaluating damage. It may be arranged so that only either one of the search coils 41F, 41R is provided.

A plate-shaped support member 60 is secured to the opposing faces of the plate-shaped yokes 32F, 32R, and a Hall device group 61 is provided inside the support member 60. The Hall device group 61 includes a plurality of Hall devices 61a arrayed linearly along the concrete surface in a direction orthogonal to the direction of the axis at the center of the excitation coil 24 (the axial direction of the tendon 10). The Hall devices 61a output voltages proportional to the strength of the magnetic field (magnetic flux density). The plurality of Hall devices 61a are all arrayed in an orientation responsive to magnetic flux along the axial direction of the excitation coil 24 through the center thereof.

The Hall devices 61a having their response orientation aligned along the axial direction of the excitation coil 24 through the center thereof are used in order to measure or confirm the strength of the magnetic field generated in the excitation coil 24. The higher the current that flows through the excitation coil 24, the greater the strength of the magnetic field generated in the excitation coil 24 and the larger the output signal from the Hall devices 61a.

Preferably, the Hall device group 61 that includes the multiple Hall devices 61a is provided at a position midway between the plate-shaped yokes 32F, 32R, namely at a position midway between the magnetic poles. Since the magnetic field at the position midway between the magnetic poles is more stable in comparison with the magnetic field at a location near either of the plate-shaped yokes 32F, 32R, the accuracy with which the strength of the magnetic field generated by the excitation coil 24 can be improved.

Figure 5:
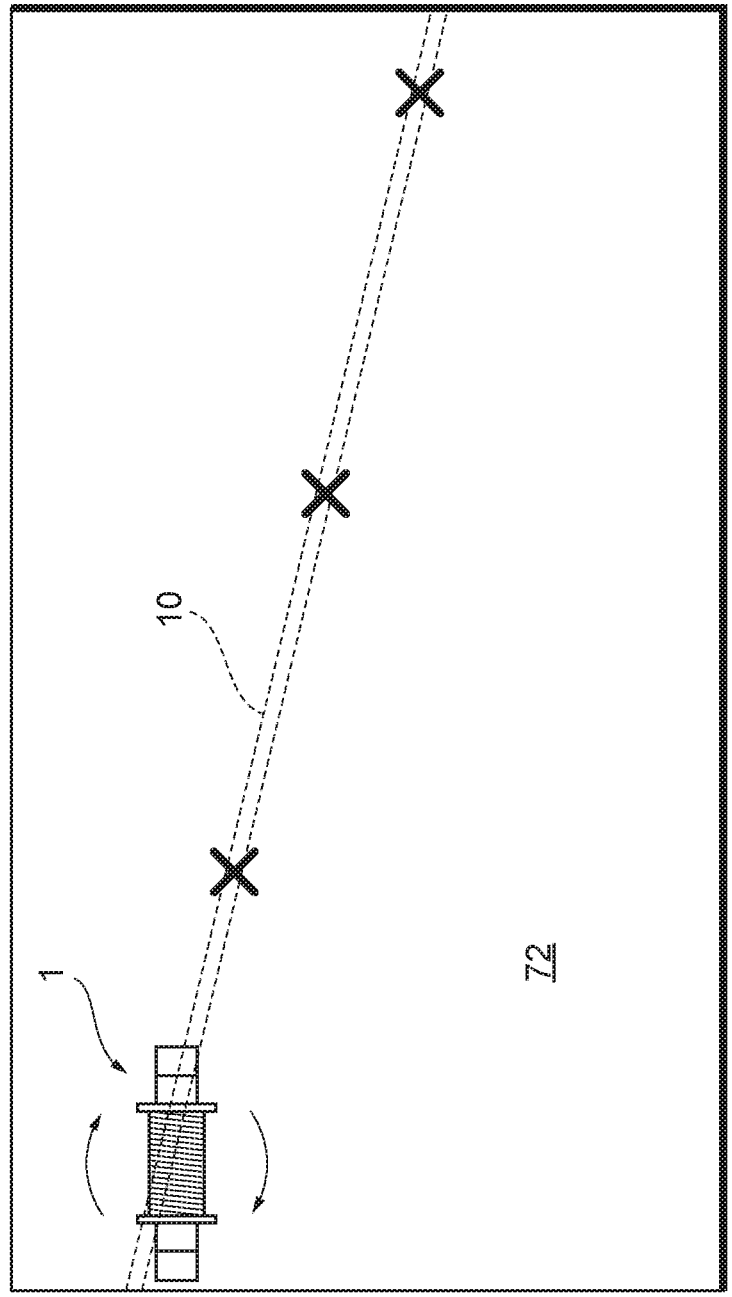
FIG. 5 illustrates the manner in which the traveling position of the damage evaluation apparatus is determined.

FIG. 5 illustrates the manner in which the path of travel of the damage evaluation apparatus 1 is determined at such time that the tendon 10 embedded in the concrete (lower flange 72) is inspected.

As mentioned above, a magnetic circuit is formed by the magnetizer 20 possessed by the damage evaluation apparatus 1 and a portion of the tendon 10 situated below the damage evaluation apparatus 1. The closer both poles of the magnetizer 20, namely the plate-shaped yokes 32F, 32R, are to the tendon 10, the larger the output signals from the search coils 41F, 41R wound around the respective columnar yokes 31F, 31R that construct the magnetizer 20. Accordingly, based upon these output signals from the search coils 41F, 41R, it can be determined whether the damage evaluation apparatus 1 (plate-shaped yokes 32F, 32R) placed on the surface of the concrete is situated directly above the tendon 10 embedded in the concrete, and whether the axial direction of the magnetizer through the center thereof and the axial direction of the tendon 10 coincide. More specifically, it will suffice if the position of placement and orientation of the damage evaluation apparatus 1 are adjusted so as to maximize the output signals from the search coils 41F, 41R. Since the damage evaluation apparatus 1 is equipped with the casters 52, as mentioned above, the damage evaluation apparatus 1 can be moved linearly along the concrete surface and can be turned by a small force as well. This alleviates the burden on the worker whose task is to adjust the direction of the damage evaluation apparatus 1 so as to position the damage evaluation apparatus 1 directly above the tendon 10 and, in addition, to make the central axis of the excitation coil 24 coincide with the axial direction of the tendon 10.

By observing the output signals from the search coils 41F, 41R at multiple locations on the concrete surface (e.g., locations marked "X" in FIG. 5 showing also the location of the damage evaluation apparatus 1), the position at which the damage evaluation apparatus 1 should be placed and the direction thereof (the embedded position and direction of the tendon 10 embedded in the concrete) can be ascertained accurately. As mentioned above, rails (not shown) for moving the damage evaluation apparatus 1 along the ascertained embedded position of the tendon 10 are placed on the concrete surface. By moving the damage evaluation apparatus 1 along the installed rails, the damage evaluation apparatus 1 can be moved while it is made to travel along the tendon 10 embedded in the concrete and, moreover, while the axial direction of the excitation coil 24 through its center continues to be made to coincide with the axial direction of the tendon 10.

Figure 6:
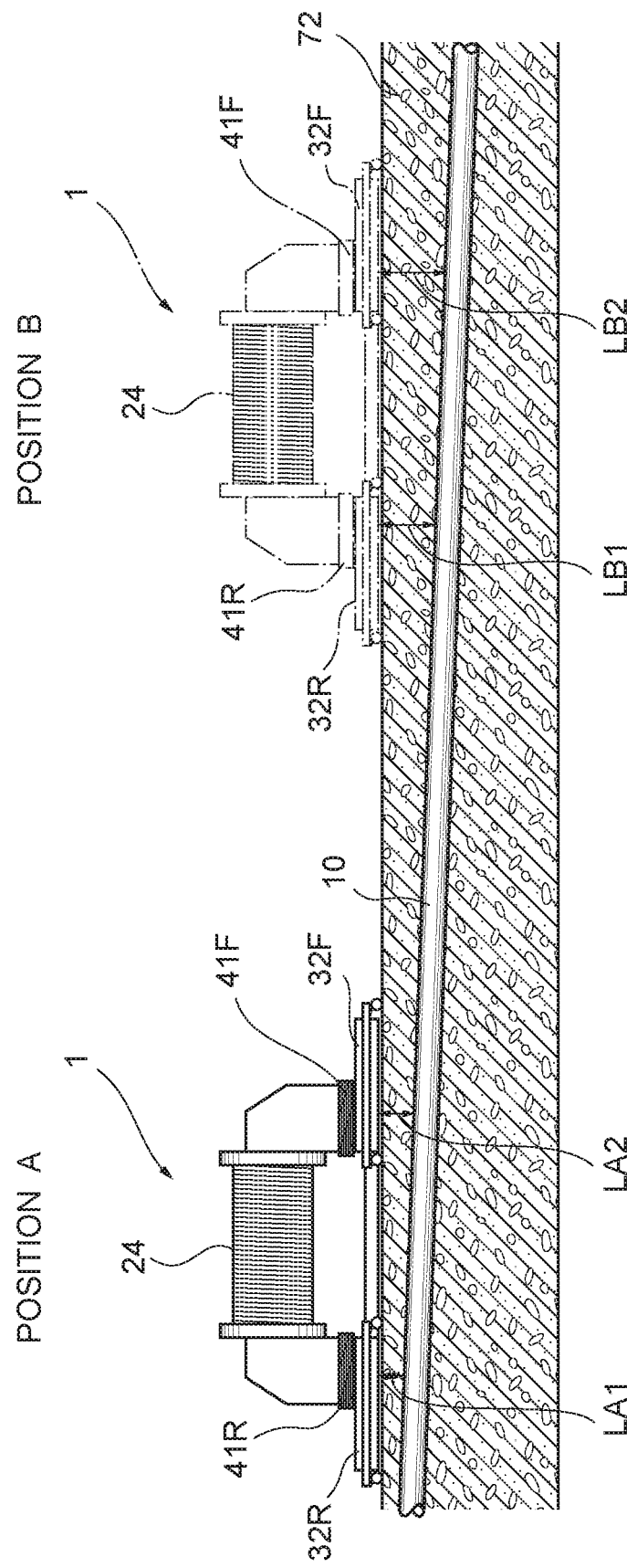
FIG. 6 illustrates how the distance between the damage evaluation apparatus and a tendon varies in dependence upon depth at which the tendon is embedded.

FIG. 6 illustrates the manner in which a gap varies when the tendon 10 has been embedded obliquely with respect to the thickness direction of the concrete (lower flange 72).

As set forth above, there are instances where the tendon 10 is embedded obliquely in the thickness direction of the concrete in order to impart the concrete with compressive stress uniformly in the thickness direction. As indicated by Equations (1) and (2) cited above, the magnetic flux of the magnetic circuit that includes the tendon 10 is inversely proportional [Equation (1)] to the magnetic resistance R of the magnetic circuit, and the magnetic resistance R is proportional [Equation (2)] to gap length L (the distance between the plate-shaped yokes 32F, 32R and the tendon 10). That is, since the magnetic flux of the magnetic circuit is inversely proportional to the gap length L, the greater the gap length L, the smaller the magnetic flux of the magnetic circuit.

The magnetic flux of the magnetic circuit when the damage evaluation apparatus 1 is situated at the location (let this be position B) indicated by the one-dot chain line in FIG. 6, namely when the embedded position of the tendon 10 is a comparatively deep position (total gap length L=LB1+LB2), is smaller than the magnetic flux of the magnetic circuit when the damage evaluation apparatus 1 is situated at the location (let this be position A) indicated by the solid line in FIG. 6, namely when the embedded position of the tendon 10 is a comparatively shallow position (total gap length L=LA1+LA2).

Figure 7:
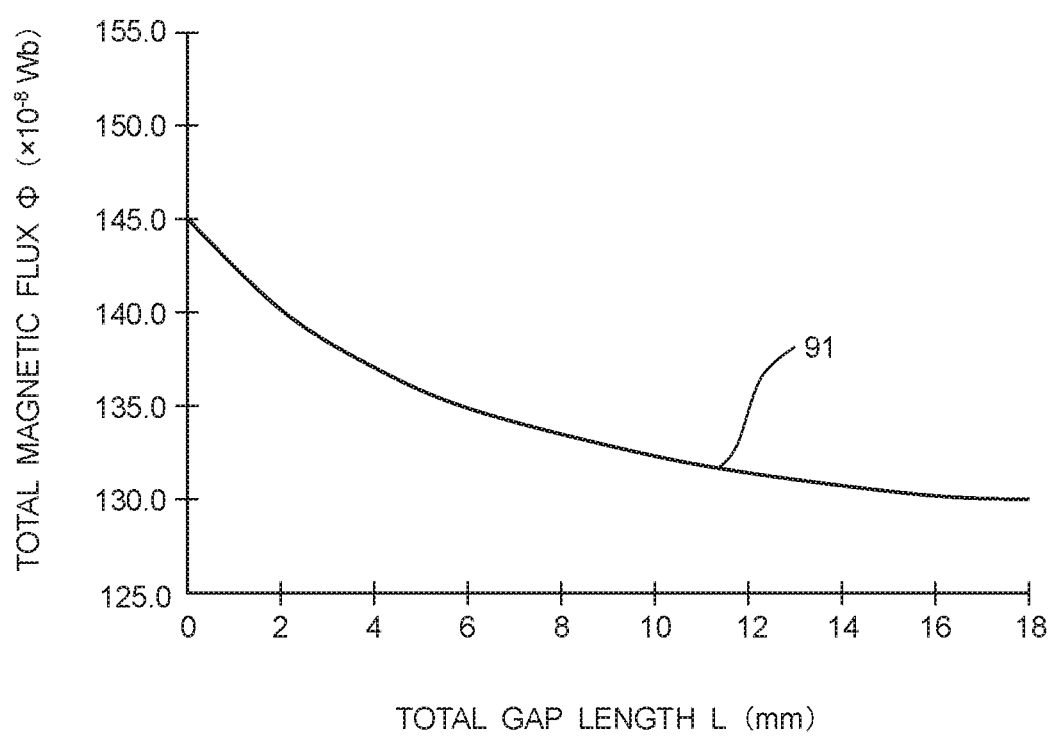
FIG. 7 is a graph illustrating the relationship between gap length and magnetic flux of a search coil when an electric current passed through an excitation coil is held constant.

FIG. 7 is a graph showing a curve 91 of the total value f of magnetic flux (indicated along the vertical axis) measured by the search coils 41F, 41R when a wire rope having a diameter of 15.2 mm is used as the tendon 10, the electric current passed through the excitation coil 24 is held constant and the total gap length L (indicated along the horizontal axis) is varied.

In view of the curve 91 shown in FIG. 7, it is confirmed that, the larger the total gap length L, namely the deeper the embedded position of the tendon 10 in the concrete, the smaller the total magnetic flux f measured by the search coils 41F, 41R.

The magnetic flux of the magnetic circuit that includes the tendon 10 can be controlled by increasing or decreasing the electric current passed through the excitation coil 24. Specifically, the magnetic flux of the magnetic circuit that includes the tendon 10 can be held constant by controlling the electric current, which is passed through the excitation coil 24, in dependence upon the embedded depth of the tendon 10.

Figure 8:
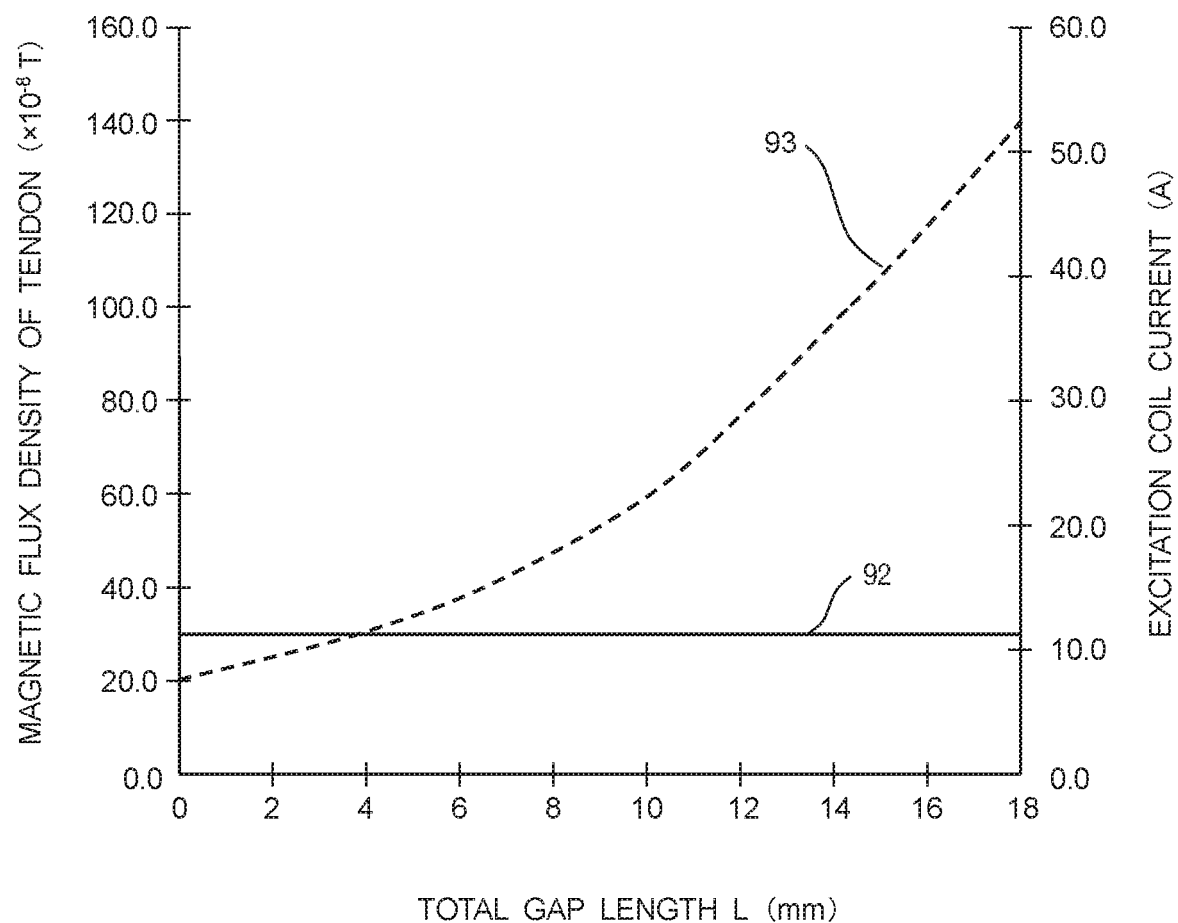
FIG. 8 is a graph illustrating electric current to be passed through an excitation coil in order to hold constant the magnetic flux of a tendon.

FIG. 8 illustrates a graph for when the electric current passed through the excitation coil 24 is controlled in such a manner that the magnetic flux density of the tendon 10 (the strength of the magnetic field in the vicinity of the tendon 10), which constitutes the magnetic circuit over the range thereof situated between the columnar yokes 31F, 31R (plate-shaped yokes 32F, 32R), will be rendered constant irrespective of the total gap length L. A solid line 92 in FIG. 8 is a plot of magnetic flux density of the tendon 10, and the broken line 93 is a plot of the current value of the electric current passed through the excitation coil 24.

In view of the curve 91 (the relationship between total gap length L and the total magnetic flux f of the two search coils 41F, 41R) of FIG. 7, the embedded depth (total gap length L) of the tendon 10 embedded in the concrete member can be determined based upon the total magnetic flux f measured by the two search coils 41F, 41R. Further, the value of the current to be passed through the excitation coil 24 in order to render constant (uniformalize) the magnetic flux density of the tendon 10 in accordance with the embedded depth (total gap length L) of the tendon 10 can be ascertained from the curve 93 (the relationship between total gap length L and the value of the electric current passed through the excitation coil 24) of FIG. 8. More specifically, by controlling the electric current passed through the excitation coil 24 using the curve 91 shown in FIG. 7 and the curve 93 shown in FIG. 8, the magnetic flux density (strength of the magnetic field) of the tendon 10 constituting the magnetic circuit can be held constant even though the tendon 10 has been embedded in the concrete obliquely in the thickness direction thereof.

With regard to the embedded depth of the tendon 10 (the distance from the concrete surface to tendon 10 embedded in the concrete), this can be measured using ultrasonic waves or impact elastic waves. In this case, the electric current passed through the excitation coil 24 can be decided in accordance with the curve 93, shown in FIG. 8, based upon the embedded depth of the tendon 10 measured using ultrasonic waves or impact elastic waves.

Figure 9A:
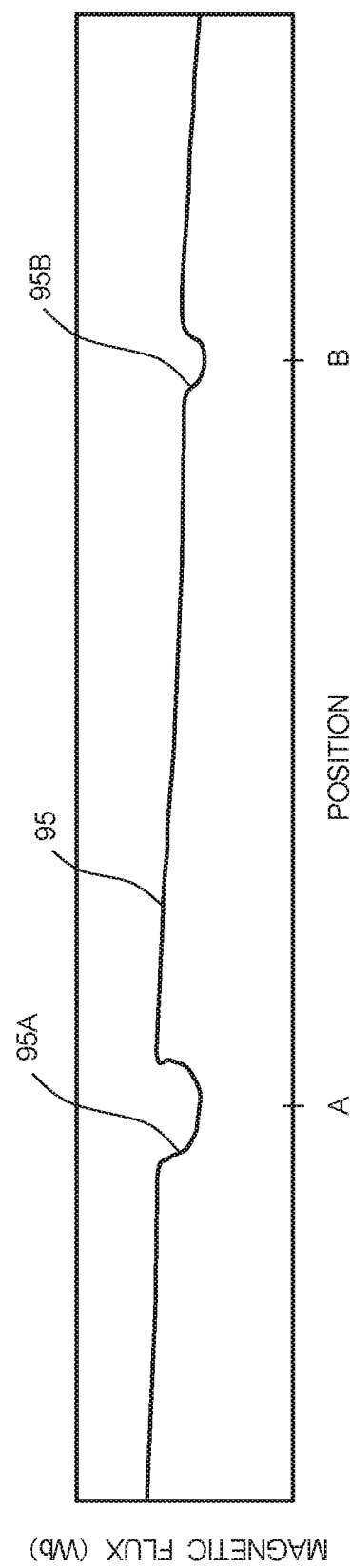
FIG. 9A is a graph of magnetic flux calculated based upon output voltages from search coils prior to processing for averaging magnetic field strength.
Figure 9B:
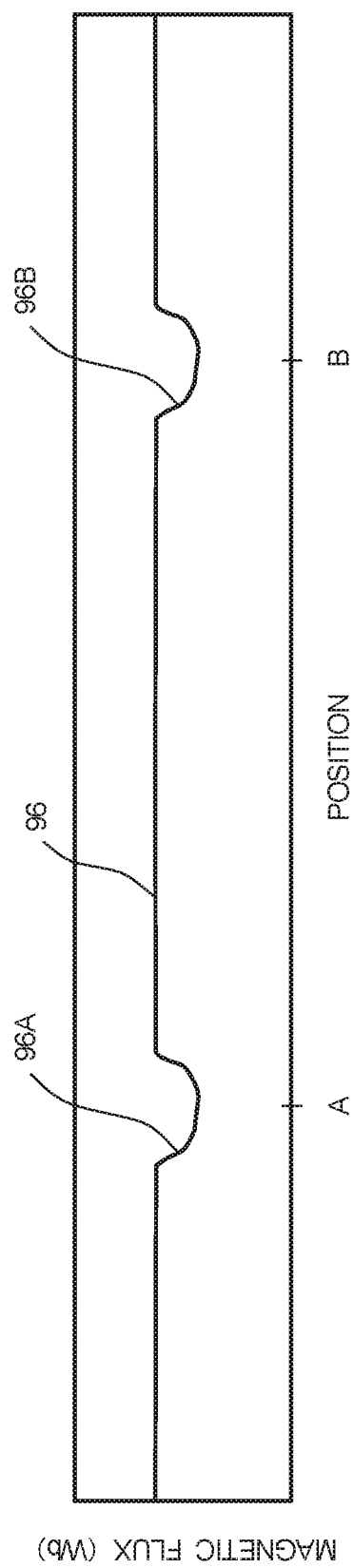
FIG. 9B is a graph of magnetic flux calculated based upon output voltages from the search coils after processing for averaging magnetic field strength.

FIGS. 9A and 9B respectively illustrate signal waveforms 95, 96 of magnetic flux (number of magnetic flux linkages) calculated based upon the output voltages from the search coils 41F, 41R when the damage evaluation apparatus 1 is moved on the surface of the concrete along the tendon 10 in a case where the tendon 10 has been embedded obliquely in the thickness direction of the concrete, as illustrated in FIG. 6, and, in addition, similar corrosion has occurred at two different locations (positions A and B) of the tendon 10. FIG. 9A illustrates the curve 95 obtained when the current passed through the excitation coil 24 is held constant, and FIG. 9B illustrates the curve 96 obtained when the current passed through the excitation coil 24 is controlled in dependence upon the embedded depth of the tendon 10, as described above. In FIGS. 9A and 9B, the horizontal axis indicates the position of the damage evaluation apparatus 1 measured by the rotary encoder 63.

If the tendon 10 is corroded, a decrease in magnetic flux is observed in the signal waveforms 95, 96 (at 95A, 95B, 96A, 96B) during the times that the corroded areas are situated between the two magnetic poles (plate-shaped yokes 32F, 32R).

With reference to FIG. 9A, in a case where the current passing through the excitation coil 24 is constant, the magnetic flux density in the tendon 10, which forms the magnetic circuit, is comparatively large when the tendon 10 has been embedded at a comparatively shallow location. A decrease in magnetic flux indicative of the corroded area, therefore, is clearly observed (reference characters 95A). If the tendon 10 has been embedded deeply, however, the magnetic flux density of the tendon 10 forming the magnetic circuit decreases (the strength of the magnetic field weakens) and therefore the decrease in the magnetic flux indicating the corroded area, as well as the amplitude of the magnetic flux, becomes smaller (reference characters 95B). Even if the extent of the damage that the tendon 10 has sustained at position A is equal to that at position B, it is difficult to judge the fact that they are the same based upon the signal waveform.

With reference to FIG. 9B, on the other hand, by controlling the electric current passed through the excitation coil 24 in such a manner that the magnetic flux density of the tendon 10 is rendered constant irrespective of the embedded depth of the tendon 10, similar signal waveforms 96A, 96B can be manifested in the signal waveform 96, regardless of whether the tendon 10 is embedded shallowly (position A) or deeply (position B), if the corrosion at these positions is similar. That is, the signal waveforms representing damage can be normalized, thereby making it possible to grasp the extent of corrosion correctly.

Figure 10:
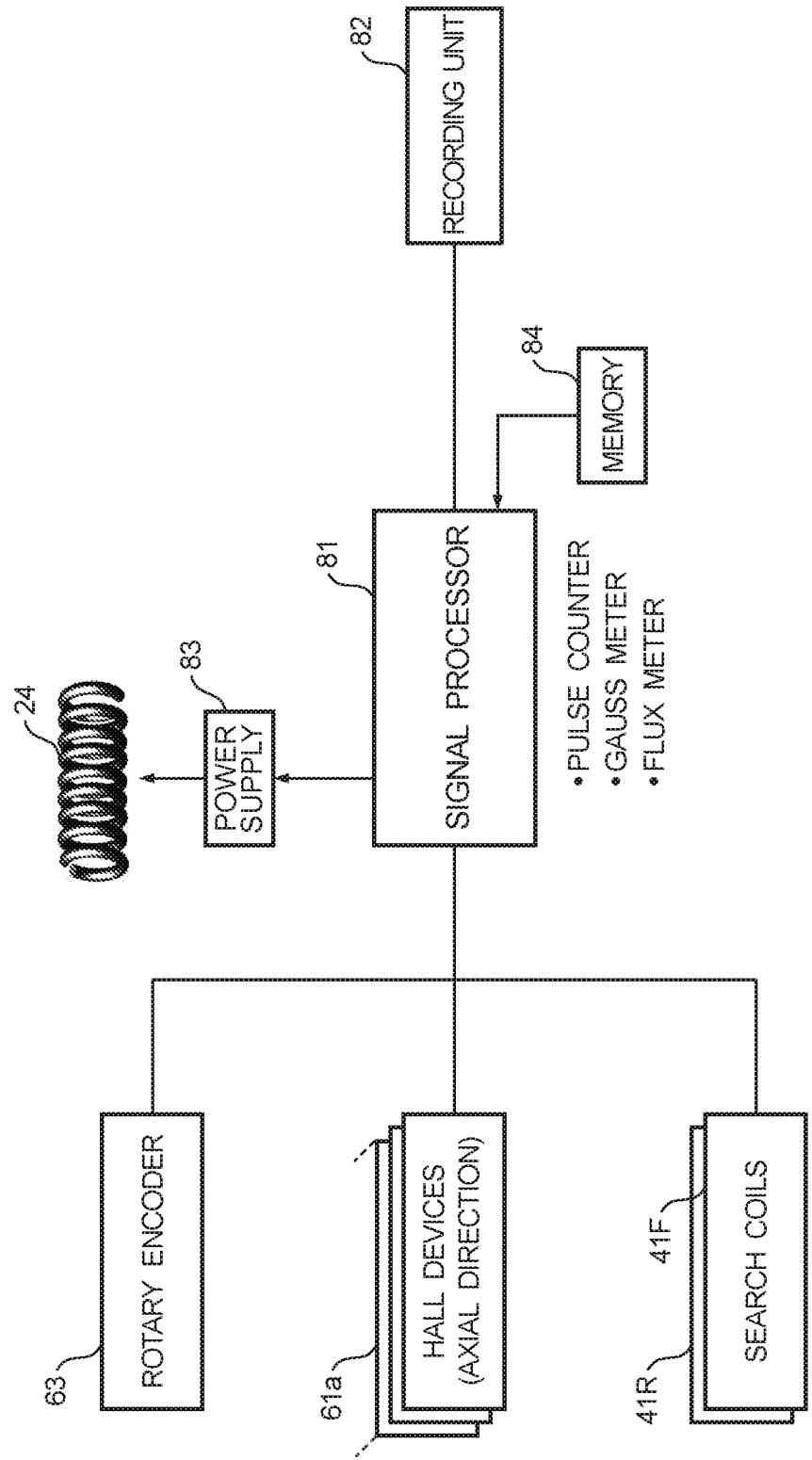
FIG. 10 is a block diagram illustrating the electrical configuration of a processing unit for processing signals output from a group of sensors.

FIG. 10 is a block diagram illustrating the electrical configuration of a processing unit for processing signals output from the group of sensors (the rotary encoder 63, the Hall devices 61a responsive to the magnetic flux in the axial direction of the tendon 10, and the search coils 41F, 41R) with which the damage evaluation apparatus 1 is equipped.

The rotary encoder 63 provided on the caster 52 for moving the damage evaluation apparatus 1 outputs a pulse signal, and the signal is applied to a signal processor 81. The signal processor 81 has a pulse counter and calculates data, which is indicative of the amount of movement of the damage evaluation apparatus 1, from the amount of movement per pulse and the number of pulses. The data indicating the amount of movement is recorded in a recording unit 82.

The Hall devices 61a are connected to a Gauss meter (Tesla meter) possessed by the signal processor 81. As mentioned above, the Hall devices 61a output voltages proportional to magnetic flux density. Based upon the output voltages from the Hall devices 61a, the signal processor 81 calculates magnetic flux density and applies it to the recording unit 82. An increase and decrease in the magnetic flux density conforming to an increase and decrease in the current passed through the excitation coil 24 can be confirmed.

The search coils 41F, 41R provided in the magnetic path of the magnetic circuit are connected to a flux meter possessed by the signal processor 81. Voltages produced in the search coils 41F, 41R owing to a change in magnetic flux are integrated over time in the flux meter, whereby the magnetic flux (number of magnetic flux linkages) is calculated. This is applied to the recording unit 82. Damage that has occurred in the tendon 10 can be determined quantitatively based upon the change in magnetic flux [see FIG. 9B].

The signal processor 81 is connected to a power supply device 83 that supplies the excitation coil 24 with electric current, and also connected is a memory 84 for storing data (FIG. 8) indicating the relationship between the above-described total gap length L and value of current to be passed through the excitation coil 24. The total gap length L (embedded depth of the tendon 10) is measured in advance when the tendon 10 is inspected, and the value of current to be passed through the excitation coil 24 is decided in accordance with the calculated total gap length L. The electric current supplied to the excitation coil 24 from the power supply device 83 is controlled by the signal processor 81 so as to render constant the magnetic flux density (strength of the magnetic field) of the tendon 10, which forms the magnetic circuit, irrespective of the total gap length L (embedded depth of the tendon 10).

The electric current may be controlled by the signal processor 81 continuously when the damage evaluation apparatus 1 is moved along the tendon 10, or it may be arranged to move the damage evaluation apparatus 1 along the tendon 10 under a constant electric current without controlling the current, identify areas where damage has occurred, and move the damage evaluation apparatus 1 at the identified areas using a large electric current commensurate with the embedded depth of the tendon 10 at the identified damage areas.

The invention claimed is:

1. A method of evaluating damage to a magnetic linear body embedded in a concrete structure, comprising:
   moving a damage evaluation apparatus along the magnetic linear body which the magnetic linear body, which is to undergo evaluation of damage, said apparatus including a magnetizer for generating magnetic force, and a detector for detecting an amount of change in magnetism produced from a damaged area of the magnetic linear body magnetized by the magnetic force generated by the magnetizer;
   forming a magnetic circuit by passing an electric current through an excitation coil by the magnetizer, wherein said magnetizer includes the excitation coil as well as a yoke shaft inserted into a center hole of the excitation coil, and a pair of columnar yokes connected to respective ones of both ends of the yoke shaft and each extending toward the surface of the concrete, the magnetic circuit including the yoke shaft, the pair of columnar yokes, and the magnetic linear body over a range thereof situated between the pair of columnar yokes; and
   controlling the electric current, which is passed through the excitation coil, in dependence upon embedded depth of the magnetic linear body within the concrete structure so as to hold constant a magnetic flux density in the magnetic linear body over the range thereof situated between the pair of columnar yokes.

2. The method of evaluating damage to a magnetic linear body according to claim 1, wherein said detector is a search coil wound around at least one of the pair of columnar yokes.

3. The method of evaluating damage to a magnetic linear body according to claim 1, wherein said damage evaluation apparatus has a position detecting device for detecting position of the damage evaluation apparatus relative to the magnetic linear body, path of movement of the damage evaluation apparatus being decided in accordance with an output from the position detecting device.

4. The method of evaluating damage to a magnetic linear body according to claim 3, wherein said position detecting device constitutes search coils wound around respective ones of the pair of columnar yokes.

5. An apparatus for evaluating damage to a magnetic linear body is used upon being placed on a concrete structure in which the magnetic linear body, which is to undergo evaluation of damage, is embedded, said apparatus comprising:
   a magnetizer for generating magnetic force, and a detector for detecting an amount of change in magnetism produced from a damaged area of the magnetic linear body magnetized by the magnetic force generated by the magnetizer;
   a moving device, which includes a movement amount sensor, for moving said damage evaluation apparatus along the magnetic linear body, and a power supply device for supplying the magnetizer with electric current;
   wherein said magnetizer includes an excitation coil, a yoke shaft inserted into a center hole of the excitation coil, and a pair of columnar yokes connected to respective ones of both ends of the yoke shaft and each extending toward the surface of the concrete, and passes an electric current through the excitation coil, whereby a magnetic circuit is formed by the yoke shaft, the pair of columnar yokes, and the magnetic linear body over a range thereof situated between the pair of columnar yokes;
   a control unit for controlling the electric current, which is passed through the excitation coil of the magnetizer from the power supply device, in dependence upon embedded depth of the magnetic linear body within the concrete structure so as to hold constant a magnetic flux density in the magnetic linear body over the range thereof situated between the pair of columnar yokes.

6. The apparatus for evaluating damage to a magnetic linear body according to claim 5, wherein said detector is a search coil wound around at least one of the pair of columnar yokes.

7. The apparatus for evaluating damage to a magnetic linear body according to claim 5, further provided with a position detecting device for detecting the position of said apparatus relative to the magnetic linear body.

8. The apparatus for evaluating damage to a magnetic linear body according to claim 7, wherein said position detecting device constitutes search coils wound around respective ones of the pair of columnar yokes.

\* \* \* \* \*